United States Patent
Cleary

(10) Patent No.: US 10,105,195 B2
(45) Date of Patent: Oct. 23, 2018

(54) ORTHODONTIC AUXILIARY AND CONNECTOR WITH MODIFIABLE ACTIVATION PARAMETERS

(71) Applicant: 3M INNOVATIVE PROPERTIES COMPANY, St. Paul, MN (US)

(72) Inventor: James D. Cleary, Glendora, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/529,553

(22) PCT Filed: Dec. 23, 2015

(86) PCT No.: PCT/US2015/000184
§ 371 (c)(1),
(2) Date: May 25, 2017

(87) PCT Pub. No.: WO2016/105466
PCT Pub. Date: Jun. 30, 2016

(65) Prior Publication Data
US 2017/0319297 A1 Nov. 9, 2017

Related U.S. Application Data

(60) Provisional application No. 62/095,909, filed on Dec. 23, 2014.

(51) Int. Cl.
*A61C 7/36* (2006.01)
*A61C 7/18* (2006.01)

(52) U.S. Cl.
CPC . *A61C 7/36* (2013.01); *A61C 7/18* (2013.01)

(58) Field of Classification Search
CPC .................................... A61C 7/36; A61C 7/18
USPC ...................................................... 433/18–19
See application file for complete search history.

(56) References Cited

U.S. PATENT DOCUMENTS

| 4,382,783 | A | * | 5/1983 | Rosenberg | A61C 7/36 |
| | | | | | 433/19 |
| 4,472,139 | A | | 9/1984 | Rosenberg | |
| 4,551,095 | A | * | 11/1985 | Mason | A61C 7/36 |
| | | | | | 433/19 |
| 4,669,979 | A | | 6/1987 | Snead | |
| 4,708,646 | A | | 11/1987 | Jasper | |
| 4,969,822 | A | | 11/1990 | Summer | |
| 5,120,218 | A | * | 6/1992 | Hanson | A61C 7/36 |
| | | | | | 433/19 |

(Continued)

FOREIGN PATENT DOCUMENTS

| DE | 29724863 | 3/2005 |
| WO | WO 2017-120078 | 7/2017 |

OTHER PUBLICATIONS

Haegglund, The Swedish-Style Integrated Herbst Appliance. Journal of Clinical Orthodontics, 1997, vol. 31, No. 6, pp. 378-390.

(Continued)

*Primary Examiner* — Nicholas Lucchesi
*Assistant Examiner* — Shannel Wright

(57) ABSTRACT

The present disclosure provides intra-oral devices for repositioning the relationship between upper and lower dental arches. The devices are attached to appliances on molar teeth of each arch and can be reactivated without removal or replacement of substantial components of the device.

13 Claims, 9 Drawing Sheets

(56) References Cited

U.S. PATENT DOCUMENTS

| | | | |
|---|---|---|---|
| 5,317,074 A | 5/1994 | Hammar | |
| 5,352,116 A | 10/1994 | West | |
| 5,435,721 A | 7/1995 | Vogt | |
| 5,651,672 A | 7/1997 | Cleary | |
| 5,678,990 A * | 10/1997 | Rosenberg | A61C 7/36 433/19 |
| 5,964,588 A * | 10/1999 | Cleary | A61C 7/36 433/18 |
| 5,980,247 A * | 11/1999 | Cleary | A61C 7/36 433/19 |
| 6,053,730 A | 4/2000 | Cleary | |
| 6,162,051 A * | 12/2000 | Brehm | A61C 7/36 433/19 |
| 6,234,791 B1 * | 5/2001 | Cleary | A61C 7/00 433/18 |
| 6,234,792 B1 * | 5/2001 | DeVincenzo | A61C 7/36 433/19 |
| 6,254,384 B1 | 7/2001 | Rosenberg | |
| 6,273,713 B1 * | 8/2001 | Liou | A61C 7/36 433/19 |
| 6,589,051 B2 | 7/2003 | Cleary | |
| 6,913,460 B2 | 7/2005 | Cleary | |
| 6,988,888 B2 | 1/2006 | Cleary | |
| 7,578,671 B2 | 8/2009 | Corcoran | |
| 7,811,087 B2 | 10/2010 | Wiechmann | |
| 8,257,080 B2 | 9/2012 | Wiechmann | |
| 8,714,974 B2 | 5/2014 | Cleary | |
| 8,932,054 B1 | 1/2015 | Rosenberg | |
| 9,402,696 B2 * | 8/2016 | Radmall | A61C 7/34 |
| 2004/0219474 A1 | 11/2004 | Cleary | |
| 2007/0020577 A1 | 1/2007 | Corcoran | |
| 2012/0028207 A1 | 2/2012 | Cleary | |
| 2012/0028208 A1 | 2/2012 | Cleary | |
| 2012/0135365 A1 | 5/2012 | Cleary | |
| 2014/0057222 A1 * | 2/2014 | Kumar | A61C 7/36 433/19 |
| 2014/0272758 A1 * | 9/2014 | Mohr | A61C 7/36 433/19 |
| 2014/0272759 A1 | 9/2014 | Dischinger | |
| 2015/0257858 A1 * | 9/2015 | Dischinger | A61C 7/36 433/19 |
| 2016/0175074 A1 | 6/2016 | Cleary | |

OTHER PUBLICATIONS

ORMCO AOA, Brochure for AdvanSync 2, pp. 2.
International Search Report for PCT International Application No. PCT/US2015/000184, dated Mar. 11, 2016, 2 pages.

* cited by examiner

ORTHODONTIC AUXILIARY AND CONNECTOR WITH MODIFIABLE ACTIVATION PARAMETERS

CROSS REFERENCE TO RELATED APPLICATIONS

This application is a national stage filing under 35 U.S.C. 371 of PCT/US2015/000184, filed Dec. 23, 2015, which claims the benefit of U.S. Provisional Application No. 62/095,909, filed Dec. 23, 2014, the disclosures of which are incorporated by reference in their entirety herein.

BACKGROUND

The field of orthodontics relates to the supervision, guidance and correction of teeth towards proper positions in the oral cavity. Orthodontic therapy generally involves the application of forces to move teeth into a proper bite configuration, or occlusion. One mode of therapy, known as fixed appliance treatment, is carried out using a set of tiny slotted appliances called brackets, which are affixed to at least the anterior, cuspid, and bicuspid teeth of a patient. In the beginning of treatment, a resilient orthodontic appliance known as an archwire is received in each of the bracket slots. The end sections of the archwire are typically anchored in appliances called buccal tubes, which are affixed to the patient's molar teeth.

When initially installed in the brackets and buccal tubes, the archwire is deflected from its original arcuate (or curved) shape, but then gradually returns to this shape during treatment. In this. manner, the archwire applies gentle, therapeutic forces to move the teeth from improper positions to proper positions. Taken together, the brackets, buccal tubes, and archwire are commonly referred to as "braces". Braces are often prescribed to improve dental and facial aesthetics, bite function and dental hygiene. In many instances, a set of brackets, buccal tubes and an archwire is provided for each of the upper and lower dental arches.

Brackets and other components of the fixed appliance system are commonly placed on the labial (i.e., near the patient's lips and cheeks) surfaces of the teeth. In recent decades, advances in the art have enabled brackets to be placed on the lingual surfaces of teeth. Accordingly, the components of the fixed appliance system, including the archwire, are disposed nearer the tongue, providing an attractive, aesthetic alternative as the appliance system is essentially hidden from view. Lingual brackets often have a customized design individually for every tooth and patient because, other than the labial surfaces of a tooth, the lingual surfaces greatly vary in shape relative to each other so that a "one size fits all" bracket shape typically cannot be used. Exemplary appliance systems that include brackets customized to the lingual surfaces of a dental arch are disclosed in U.S. Pat. No. 7,811,087 (Wiechmann et al.).

During certain stages of treatment, additional intraoral appliances may be prescribed for use in conjunction with fixed appliances to correct particular kinds of malocclusions. For example, some appliances are used to correct Class II malocclusions, such as an overbite where the mandibular first molars are located excessively distal (in the rearward direction) with respect to the maxillary first molars when the jaws are closed. Other appliances remedy an opposite malocclusion, known as a Class III malocclusion, such as an underbite where mandibular first molars are located excessively mesial (in the forward direction) with respect to the maxillary first molars when the jaws are closed.

In recent years, Class II and Class III correctors have been developed that are installed by the orthodontist and require minimal patient intervention during the course of treatment. These devices advantageously correct Class II and Class III malocclusions without need for patient compliance as with prior common head gear. A number of intra-oral devices for correcting Class II and Class III malocclusions are known in the art. For example, U.S. Pat. Nos. 4,708,646, 5,352,116, 5,435,721, 5,651,672, 5,964,588 and 8,257,080 describe intra-oral bite correctors with flexible and/or telescoping members that are connected to upper and lower arches of a patient. A bias tends to urge the members toward a normally straight orientation and provide a force that pushes one dental arch forward or rearward relative to the other dental arch when the jaws are closed.

As the position of the jaws is corrected, that bias is reduced during jaw closure and consequently provides less force in compression. In response, the practitioner may elect to increase the effective, active length of the intra oral device to ensure that the force exerted on the patient's jaws remains effective during the course of treatment. The effective length is typically increased or otherwise modified by removing the intra-oral device from the patient's mouth and then changing the components to continue treatment. Alternatively, stops or collars can be added to such devices to reduce the length of travel and increase the active force supplied.

Moreover, there are various possibilities in connecting these devices to the dental arch. Banded headgear tubes are still commonly used to provide a distal connection to the upper dental arch. These banded appliances, however, are not universally beloved. Bondable molar appliances are more convenient to use with labial systems in many respects and some orthodontists prefer them over banded appliances. As another option, connection to the dental arch may be made indirectly by coupling the intraoral device to one or both archwires.

SUMMARY

Though myriad products and solutions exist for attaching the Class II and Class III correctors to labial braces, the same cannot be said for lingual appliance systems. Typical methods of attachment are reliant on the presence of an archwire and other appliances on the labial surfaces of the patient's dental arches to provide an anchor for the outer end of the corrector. In present lingual appliance systems, the archwire is located proximate the lingual surfaces of the tooth, rendering attachment of the outer end loop impossible without further intervention. Moreover, it can be an advantage to connect such intra-oral devices to the molar teeth of both arches, because the relatively large size of the roots of the molar teeth provides a good anchoring location for applying forces to move one jaw relative to the other jaw.

The present disclosure provides assemblies allowing for secure use of intra-oral devices, particularly bite correctors, with labially or lingually bonded appliance systems. The assemblies serve to reduce the profile of labially attached bite intra-oral devices during use; increasing patient comfort and likely compliance with the prescribed treatment. Furthermore, the assemblies minimize the distance between the attachment mechanisms on each dental arch to ensure molar-to-molar attachment with efficient use of space. Incidentally but advantageously, the molar to molar connection also provides a more aesthetic option for the patient, as the mesial end portion of the connector is positioned at location more distal relative to the social, anterior teeth.

In particularly advantageous aspects, the present disclosure provides a connector that reduces or eliminates the need to remove the entire intra-oral device from the patient's mouth to modify the active force provided by the device. Instead, the connector may be partially decoupled and rotated to apply a different attachment length for the intra-oral device, increasing or decreasing the active force as prescribed or desired. No other component of the device need be dissembled.

In a first aspect, the present disclosure provides an intraoral force module assembly configured for moving the relative positions of upper and lower dental arches. The force module comprises a first member having a first outer end portion and coupled to a helical compression spring coaxial with at least a portion of said first member, the first member having a length extending in a generally mesial direction. The force module also includes a second member connected to the first member and pivotally movable relative to the first member in directions along a reference axis, a portion of the second member extending distally to a second outer end portion along a portion of the length of the first member. The assembly further includes a first connector connected to the second outer end portion of the second member. The second member is movable in an arc relative to the first connector about a first axis that is generally perpendicular to the reference axis and the connector is moveable between a first orientation and a second orientation, with the spring having a first active force in the first orientation and second active force in the second orientation.

In one aspect, the present disclosure provides an intraoral force module assembly configured for moving the relative positions of upper and lower dental arches. The force module comprises a first member having a first outer end portion, the first member having a length extending in a generally mesial direction. The force module also includes a second member connected to the first member and pivotally movable relative to the first member in directions along a reference axis, a portion of the second member extending distally to a second outer end portion along a portion of the length of the first member. The assembly further includes a rotatable first connector connected to the second outer end portion of the second member, wherein the second member is movable in an arc relative to the first connector about a first axis that is generally perpendicular to the reference axis, and wherein the connector is rotatable between a first orientation and a second orientation, the second orientation providing for a more distal location of the outer end portion relative to the first orientation.

The present disclosure also provides another intraoral assembly configured for moving the relative positions of upper and lower dental arches, the assembly comprising: a first orthodontic molar appliance adapted for connection to a tooth; a repositioning device comprising an upper module pivotally coupled to a lower module, wherein the upper module including a telescoping assembly having a first member and a second member slidably coupled to the first member for movement along a reference axis, the second member having an outer end portion; and the lower module including a housing defining a cavity, a portion of the housing extending distally to a second outer end portion along a portion of the length of the telescoping assembly, wherein the housing segment includes a tension member received in the cavity, and wherein the tension member is in tension and extends in length as the upper and lower dental arches are opened.

In another aspect, the present disclosure provides a method for modifying the activation force of an intraoral force module. The method comprises providing a force module including a first member having a first outer end portion, with the first member having a length extending in a generally mesial direction. The force module further includes a second member connected to the first member and pivotally movable relative to the first member in directions along a reference axis, a portion of the second member extending distally to a second outer end portion along a portion of the length of the first member. A rotatable first connector is connected to the second outer end portion of the second member and including first and second channels disposed adjacent opposing edge regions of connector, wherein the second member is movable in an arc relative to the first connector about a first axis that is generally perpendicular to the reference axis, and wherein the second member includes a rotation stop received in the first channel in the first connector. The method further includes disengaging the rotation stop from the first channel, rotating the connector to a second orientation whereby the first channel is rotated to a position distal to the second channel, and securing the rotation stop in the second channel.

In yet another aspect, the present disclosure provides a method for modifying the activation force of an intraoral force module. The method includes providing a force module with a first member having a first outer end portion, the first member having a length extending in a generally mesial direction, a second member connected to the first member and pivotally movable relative to the first member in directions along a reference axis, a portion of the second member extending distally to a second outer end portion along a portion of the length of the first member, and a first connector connected to the second outer end portion of the second member and including first and second channels separated by a channel distance adjacent opposing edge regions of connector, wherein the second member is movable in an arc relative to the first connector about a first axis that is generally perpendicular to the reference axis, and wherein the second member includes a removable first rotation stop having a first length received in the first channel in the first connector. The method further includes providing a second rotation stop having a second length, disengaging the first rotation stop from the first channel and the second member, and securing the second rotation stop in the second channel and on the second member.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a", "an," and "the" are not intended to refer to only a singular entity, but include the general class of which a specific example may be used for illustration. The terms "a", "an", and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" unless specifically stated otherwise. As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

As used herein: "Mesial" means in a direction toward the center of the patient's curved dental arch; "Distal" means in a direction away from the center of the patient's curved dental arch; "Occlusal" means in a direction toward the outer tips of the patient's teeth; "Gingival" means in a direction toward the patient's gums or gingiva; "Facial" means in a direction toward the patient's lips or cheeks; and "Lingual" means in a direction toward the patient's tongue.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

While the above-identified figures set forth several embodiments of the disclosure other embodiments are also contemplated, as noted in the description. In all cases, this disclosure presents an invention by way of representation and not limitation. It should be understood that numerous other modifications and embodiments can be devised by those skilled in the art, which fall within the scope and spirit of the principles of the inventions.

DETAILED DESCRIPTION OF EXEMPLARY EMBODIMENTS

Figure 1:
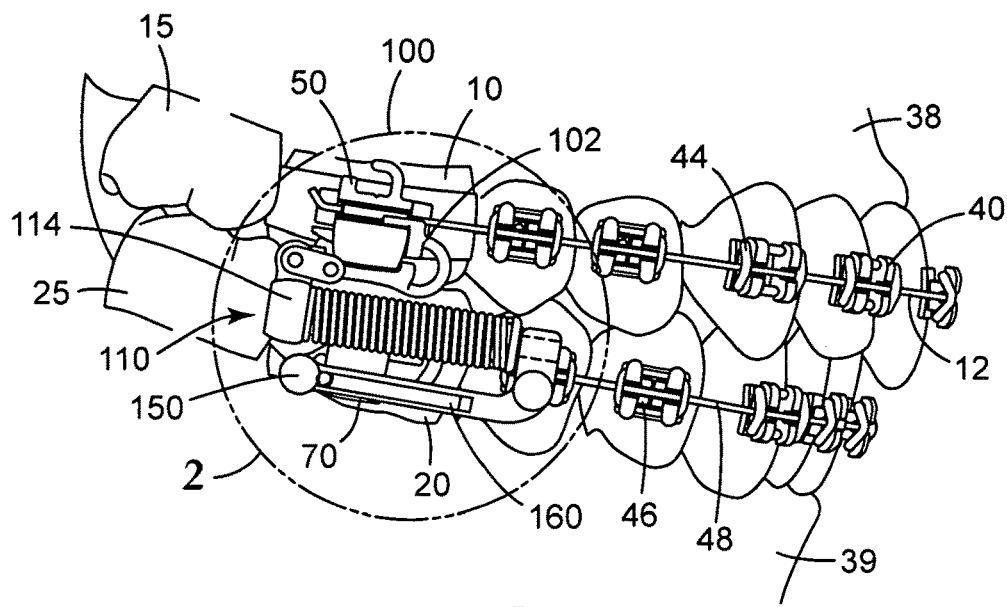
FIG. 1 is a side elevational view of an exemplary upper and lower dental arch of a patient undergoing orthodontic treatment that includes the use of a labial bracket system and an interarch force module, with the force module including both an upper module and a lower module.
Figure 2:
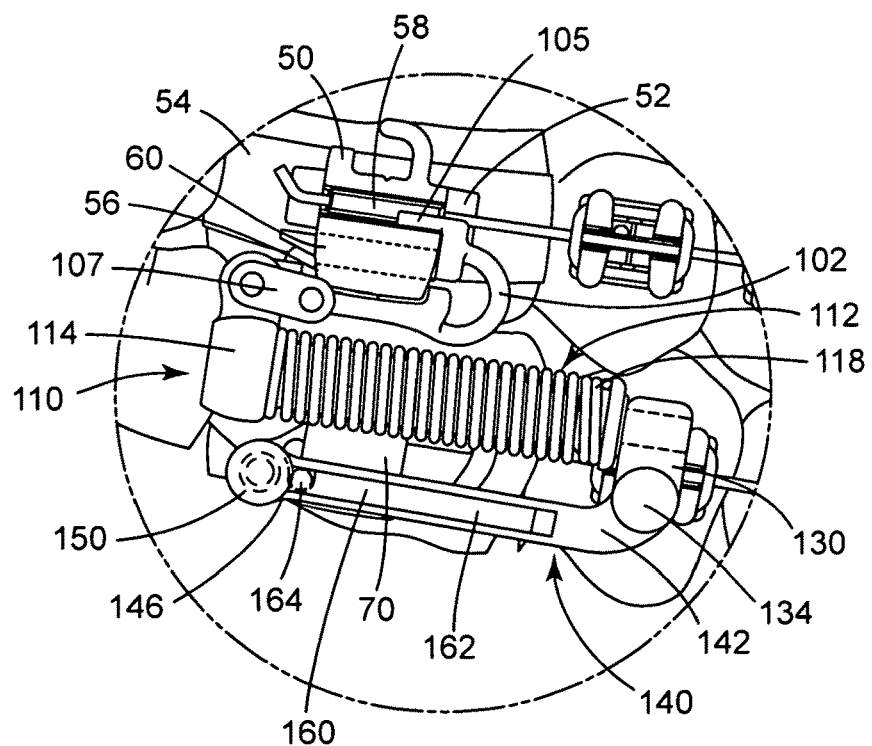
FIG. 2 is an enlarged elevational view of the interarch force module depicted in FIG. 1, looking at the force module in a lingual direction.

An exemplary embodiment of an intraoral appliance system is shown in FIGS. 1 and 2. These figures depict an orthodontic assembly, which is designated herein by the numeral 100, coupled to a set of labial brackets. The assembly 100 is installed on the right side of the upper and lower jaws (38, 39) of a patient, which are illustrated in profile view. As shown, the teeth of the upper jaw 38 include an upper central, upper lateral incisor, upper cuspid, upper first bicuspid, upper second bicuspid, upper first molar 10, and upper second molar 15. Similarly, the teeth of the lower jaw include a lower central, lower lateral, lower cuspid, lower first bicuspid, lower second bicuspid, lower first molar 20 and lower second molar 25.

A number of slotted orthodontic appliances (i.e., brackets) 40 are fixed to the teeth of the patient's upper jaw 38 and an archwire 42 is received in the archwire slot of each appliance 40. An elastomeric O-ring ligature 44 extends around tiewings of each bracket 40 in order to retain the archwire 42 in the archwire slots of the brackets 40. Similarly, a number of slotted orthodontic brackets 46 are fixed to the teeth of the patient's lower jaw 39. An archwire 48 is received in the slot of each bracket 46. An elastomeric O-ring ligature extends around the tiewings of each bracket 46 in order to retain the archwire 48 in the archwire slots of the brackets 46. In this example, both upper and lower wires 42, 48 have generally rectangular cross-sections in planes perpendicular to their longitudinal axes. Other archwire configurations, including ovular and circular cross-sections, are also possible.

The right distal ends of the upper and lower archwires 42, 48 are received in an archwire slot of molar appliances 50, 70, respectively. Optionally, an end section of the archwire 42, 48 is bent as shown in FIGS. 1 and 2 in a location adjacent the distal side of the molar appliance 50, 70. Each bracket and molar appliance includes a base or other surface for bonding the appliance to the facial surface of its respective tooth.

The upper molar appliance 50 includes a base 52. In the illustrated example, the base 52 is affixed to a band 54. The band 54 encircles the patient's upper right first molar tooth 10 and is connected to the upper molar appliance 50 by a weld or a braze joint. Optionally, the upper molar appliance 50 may be connected to the molar tooth 10 by other means such as an adhesive bond between the base 52 and the enamel surface of the molar tooth 10. The upper molar appliance 50 has a body 56 that extends outwardly from the base 52 in a generally facial direction and includes an archwire slot 58. As depicted in FIGS. 1 and 2, the appliance 50 is a convertible appliance with a section of material covering a buccal opening of the archwire slot. The body 56 includes a passage 60 adjacent the archwire slot 58. In certain implementation further described herein, the passage 60 is used in coupling a force module 110 to the upper molar appliance 50. In embodiments featuring a patient with lingual braces, the molar tube appliance need only include a base and tubular passage; the archwire slot will be unnecessary. The lower molar appliance 70 may include some or all of the same features as the upper molar appliance 50 (including convertibility), but will typically include a base, body, archwire slot, and passage.

The assembly 100 includes a combination of elements that cooperate in applying a therapeutic force between the upper and lower dental arches. In the embodiment shown, the assembly 100 includes an upper attachment device 102, a force module 110, and a lower connector 150. As depicted in FIGS. 1 and 2, the upper attachment device 102 is coupled to the passage 60 in the upper molar appliance 50. On opposite arch, the force module 110 is coupled to the lower connector 150, which is itself coupled to a passage 80 in the lower molar appliance 70.

As shown in more detail in FIG. 2, the attachment device 102 includes a first post that extends through the opening of an end cap 114 on force module 110. The first post is pivotally movable in the opening and enables pivotal movement of the attachment device 102 relative to the force module 110 in an arc about a facial-lingual reference axis. The attachment device 102 also includes a second post that is spaced from and parallel to the first post. A flat, oval-shaped plate 107 is coupled to the outer ends of both posts and serves to retain the attachment device 102 in secure, coupled relationship to the end cap 114.

The attachment device 102 typically includes at least one resilient portion that enables the attachment device 102 to couple to the upper molar tube appliance 50 in a "snap-fit" relationship. This "snap-fit" relationship is similar to the "snap-fit" relationship described in connection with the orthodontic attachment modules and couplings described in U.S. Pat. No. 6,913,460 (Cleary et al.) and U.S. Pat. No. 8,714,974 (Cleary). The resilient portions tend to hold the attachment device 102 in place and in captive relationship to the molar tube appliance 50 during the course of treatment, but also enable the attachment device 102 to be disconnected from the molar tube appliance 50 when desired.

In presently preferred circumstances, the attachment device 102 includes at least one rotation stop 105 that helps limit undue rotational movement of the attachment device 102 and the connected force module 110 about a reference axis extending in a generally mesial-distal direction. In certain circumstances, the attachment device 102 includes two rotation stops that are movable relative to each other in order to facilitate placing the rotation stops in certain beneficial operative positions adjacent wall structures of the molar tube appliance 50 for further limiting undue rotational movements. Additional aspects and alternative constructions regarding the attachment device 102 are set out in the aforementioned U.S. Pat. No. 8,714,974 (Cleary), particularly the connectors depicted in FIGS. 11 and 12 of that application. As additional alternatives, a force module 110 may be coupled to the upper arch by the connector described in US Publication No. 2012/0028207 (Cleary et al.), which features connectors coupled to an upper wire between the upper second bicuspid bracket and the upper molar tube. In operation, such alternative connectors slide distally along the wire until bearing against the mesial side of molar tube, while the third member of a force module slides mesially along the lower archwire until it bears against the distal side of a lower arch bracket.

The force module 110 shares certain aspects with the devices described in U.S. Pat. Nos. 5,964,588 and 8,714,974 (Cleary). In brief, the force module 110 includes a mesially extending upper arch module 112 pivotally coupled to a lower arch module 140. The upper arch module 112 includes a first elongated tubular member 113 and a second elongated cylindrical member 120 that is received in the first member 113 in sliding, telescoping relation. The upper arch module 112 is pivotally coupled to a lower arch module 140, which includes a third member 142 that extends distally along at least a portion of the upper module. A helical compression spring 118 extends around the first tubular member 113 and has an outer end that bears against a distal end cap 114 of the force module that is fixed to the first member 113. The opposite end of the spring 118 bears against an annular fitting that is secured to an outer end section of an inner sleeve 116.

Figure 3:
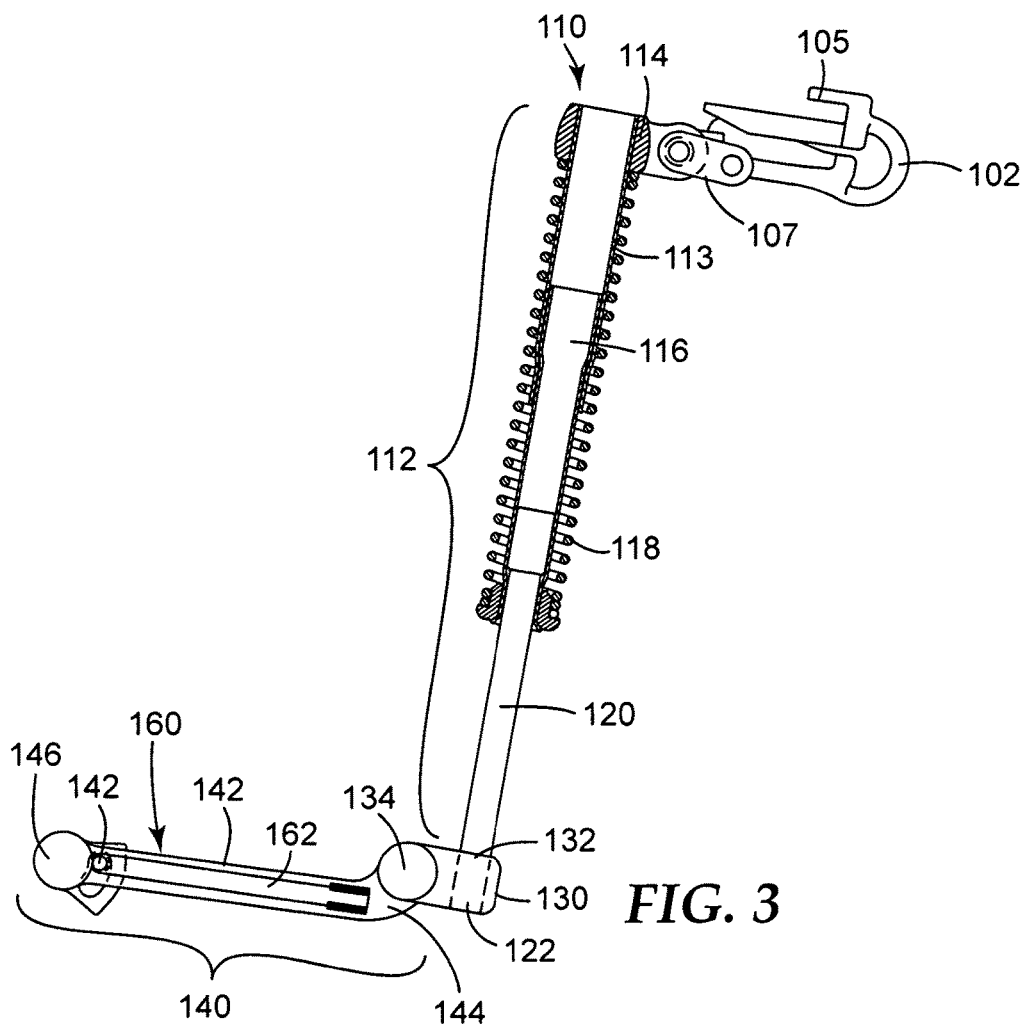
FIG. 3 is a side cross sectional view of the intra-oral force module illustrated in FIG. 1 in an open position, except that only the upper module is shown in cross section.

A cross-sectional view of the upper module 112 is set out in FIG. 3. The upper arch module 112 including a hollow first member 113 having a tubular, elongated shape. An outer end portion of the first member 113 includes an end cap 114 with an outwardly extending tab that has a circular opening to enable connection of the upper module 112 to the attachment device 102. The upper arch module 112 also includes a second member 120 received at least partially in the first member 113. The second member 120 in this embodiment includes a solid, cylindrical rod extending in a generally mesial direction towards an outer end segment or coupling portion 122. In certain embodiments, the second member 120 can include one or more collars that are fixed in place relative to the outer end segment 122. The collar can limit the extent of movement of the second member 120 in directions toward both the end cap 114 and a central pivot link 130.

With reference again to FIG. 3, the upper arch module 112 can optionally include a sleeve 116 that is preferably made of a cylindrical section of tubular material. The sleeve 116 is partially received in the first member 113 in sliding, telescoping relation. The sleeve 116 is movable relative to the first member 113 from a fully compressed position and to an extended position as shown in FIG. 3.

The sleeve 116 has an inner, enlarged end portion with an outer diameter that is larger than the outer diameter of the remaining extent of the sleeve 116. This inner end portion of the sleeve 116 has an outer diameter that is larger than the inner diameter of the mesial end portion of the first member 113 remote from the end cap 114. As such, the inner end portion of the sleeve 116 functions as a stop to limit outward movement of the sleeve 116 relative to the first member 113 and also to prevent separation of the sleeve 116 from the first member 113.

The upper arch module 112 further includes a helical compression spring 118 that extends externally around the first member 113 and the sleeve 116. An outer end of the spring 118 bears against the end cap 114 and an opposite end of the spring 118 is received in a circular recess of a connector that is fixed to an outer end portion of the sleeve 116, if used. The spring 118 is illustrated in its nearly fully compressed position in FIGS. 1 and 2 and in its relaxed and extended position in FIG. 3.

The second member 120 is partially received in the sleeve 116 and is movable in telescopic fashion in a longitudinal direction along the central, longitudinal axis of the sleeve 116 and first member 113. Preferably, the second member 120 has an outer diameter that is slightly smaller than the inner diameter of the sleeve 116 in order to allow the second member 120 to slide freely in the sleeve 116. Preferably, the adjacent end of the second member 120 is flush with the outer end of the first member 113 adjacent the end cap 114 when the force module 110 is nearly fully compressed as shown in FIGS. 1 and 2 so that the second member 120 can function to push food debris or the like out of the end cap 114.

As shown in more detail in FIG. 3, a pivot link 130 includes a generally planar segment including a mesial-distal extending passage 132 and a generally facial-lingual extending hinge 134. The pivot link 130 connects the mesial end portion of the upper module 112 to the mesial end portion of the lower arch module 140. In the depicted embodiment, the outer mesial end 122 of the second member 120 is received in the passage 132. In presently preferred circumstances, the outer mesial end 122 remains essentially fixed relative to passage 132 during use. In certain implementations, the outer mesial end 122 is permanently secured in the passage 132 via adhesive, soldering composition, or the like. In other implementations, the second member 120 is removably secured to the pivot link 130, such that the second member 120 can be replaced or modified (e.g., by inclusion sliding collars between the spring 118 and the passage 132) as desired during treatment. A removable connection between the second member 120 and the passage 132 can allow a treating practitioner to change the activation length of the force module 110 as desired.

The mesial outer end portion 144 of a segment 142 of the lower module 140 is pivotally coupled to the link 130 at hinge 134. Hinge 134 may be created by a rivet, pin, or like structure that extends through a portion of the planar pivot link 130 and the outer end 144 of a segment 142. As another example, the hinge 134 may comprise a machine screw and threaded nut which optionally may be disconnected for separation of the modules 112, 140 as desired. Other types of pivots and hinges may also be employed. Regardless of the structure used to create hinge 134 and couple the upper and lower modules, the axis of rotation created by hinge 134 extends transversely to the longitudinal axis of upper module in a generally facial-lingual direction.

The lower module 140 includes a third segment 142 that extends distally from the pivot link 130 along a longitudinal axis that is generally parallel to the longitudinal axis of the spring 118 when the assembly 100 is in the compressed configuration of FIGS. 1 and 2. The third segment 142 is generally L-shaped, with the base of the "L" corresponding to the outer end segment 144. The L-shape tends to offset the third segment 142 in a gingival direction from the spring 118 when the patient's jaws are closed, preventing interference between upper and lower components of the force module 110. In presently preferred circumstances, the third segment 142 has a generally rectangular cross-section as it extends toward distal end segment 146. In other implementations, the third segment 142 may comprise circular, ovular, square, or other cross-sectional geometries along its longitudinal axis.

Figure 4:
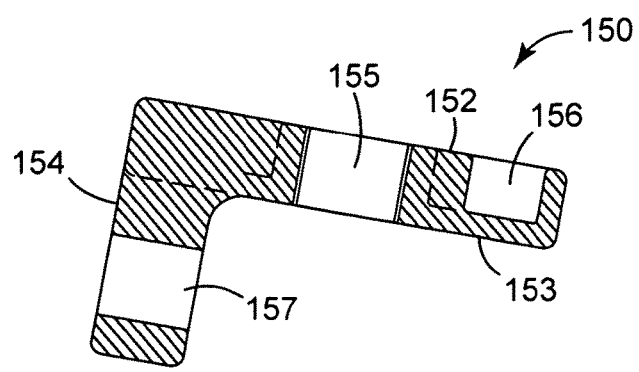
FIG. 4 is a cross-sectional view of the lower appliance connector of FIGS. 1-3.

The third segment 142 is coupled to a lower molar appliance 70 via connector 150, which allows for controlled rotation of the third segment 142 relative to the patient's lower arch. As shown in greater detail in FIG. 4, the lower connector 150 includes a base plate 152 and a coupling wall segment 154 that extends in a lingual direction at an angle of generally 90 degrees relative to the plane of the base plate 152; this present a 'L"-shape in cross-section. In the depicted embodiment, both the base plate 152 and the wall 154 include apertures 155, 157 used to align and couple the connector to the third segment 142 and the lower molar appliance 70, respectively. The base plate 152 is generally planar and extends across at least portion of the facial surfaces of the lower molar appliance 70 when secured thereto, as shown in FIG. 5.

An arcuate channel 156 is disposed in an edge region 153 of the connector 150. As explained in more detail below, the arcuate channel 156 may cooperate with a rotation stop on the lower module 140 to control rotational travel of the lower module 140 as the patient's jaws are opened. As depicted, the arcuate channel 156 does not extend through the entire thickness of base plate 152 and includes a bottom wall portion. In other embodiments, however, the channel 156 may not include a bottom wall and accordingly extend entirely through base plate 152. The channel 156 includes occlusal and gingival ends to limit rotational movement of the lower module 140 in an arc about the base plate 152 that is in the range of about 20 degrees to about 70 degrees, in some embodiments 25 degrees to about 60 degrees, and in certain implementations is in the range of about 30 degrees to about 50 degrees. These limits can prevent the lower module 140 from interfering with the patient's soft, ginvigal tissue when the patient's jaws are closed and can prevent mesial-distal reversal or destruction of the pivot link as patient's jaws are opened.

Figure 5:
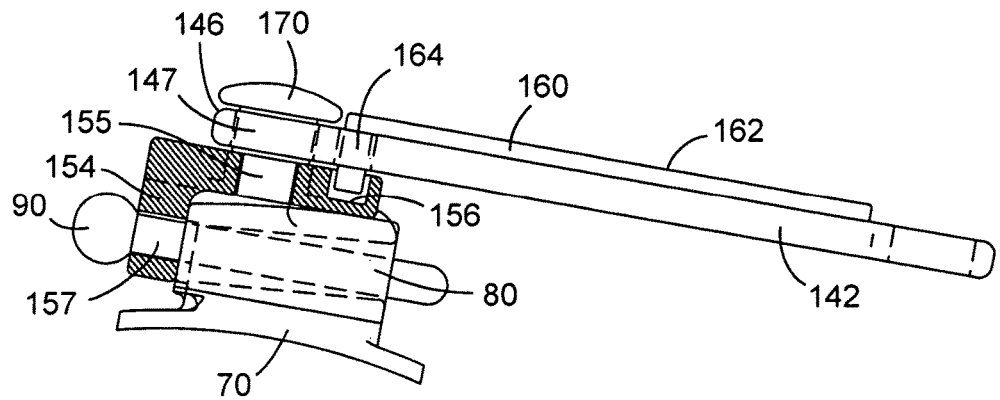
FIG. 5 is a cross-sectional view of the lower appliance connector of FIG. 4 coupled to both the lower module and a lower molar appliance.
Figure 6:
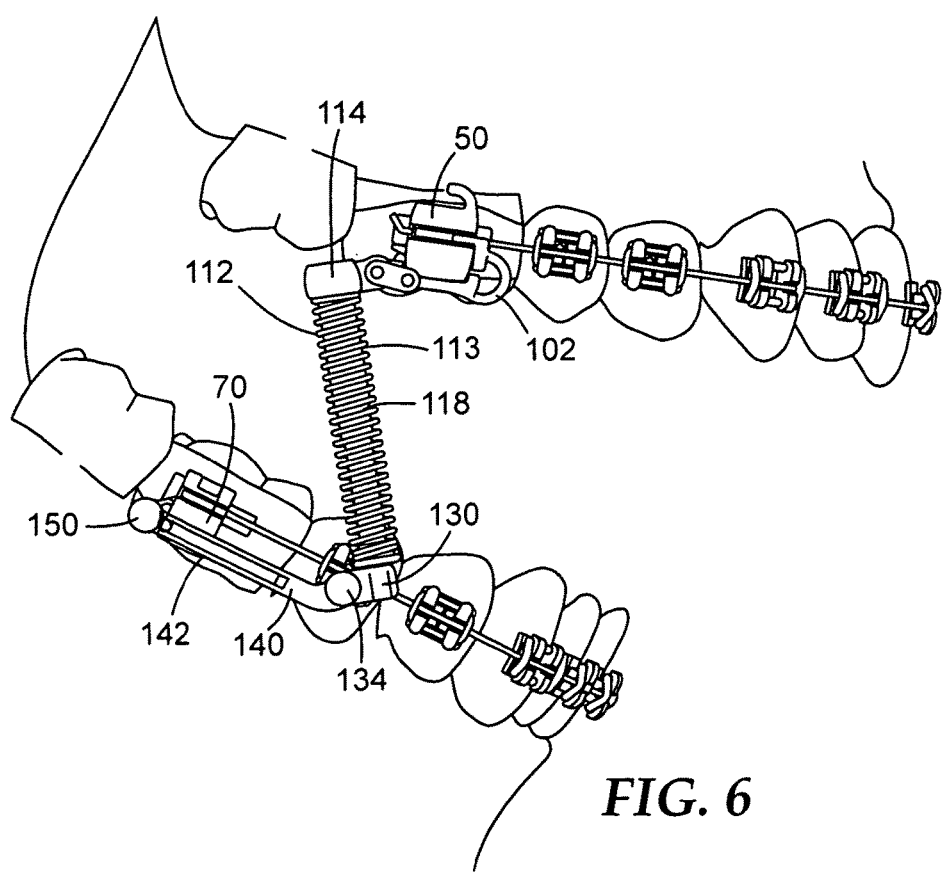
FIG. 6 is a view somewhat similar to FIG. 1 except that the patient's jaws have been partially opened.

Turning to FIG. 5, the third segment 142 terminates in a distal end coupling 146, which is configured to permit rotatable attachment of the third segment 142 to the connector 150. The end coupling 146 includes an aperture 147 that can be aligned with central aperture 155. A rivet 170 can be pressed through the aligned apertures 147, 155 to secure the respective components. As another example, aperture 155 may include interior threads, allowing a screw having corresponding threads to pass through aperture 147 and be threaded into aperture 155. To connect the distal end coupling 146 to the connector 150, the aperture 147 is placed over the corresponding aperture 155 in connector 150 and a rivet 170 is pressed, threaded or otherwise introduced into the aligned apertures 147, 155. The rivet 170 covers a portion of the distal end coupling 146 adjacent the aperture 147 in order to releasably retain the third segment in connected relation to the connector 150. In presently preferred iterations, the rivet 170 and both the aperture 147, 155 have circular cross-sectional shapes, allowing a rotational connection to be established between the connector 150 and the third segment 142.

The third segment 142 further optionally includes a rotation stop 160 for engagement with arcuate channel 156 to prevent undesired rotation of the force module as the patient's jaws are opened. In the embodiment depicted in FIGS. 1-7, the rotation stop 160 includes an elongated shaft 162 and a stop pin 164, though other configurations are possible. One end of the shaft 162 is secured towards the mesial end portion 144 of the third segment 142, remote from the distal end coupling 146. The opposite, distal end of the shaft is positioned, when secured to the connector 150, in a generally buccal direction from arcuate channel 156. In other embodiments, the rotation stop 160 may be secured to a lingual surface of the third segment 142. The stop pin 164 extends in a lingual direction from the distal end of the shaft, and is dimensionally configured for receipt in channel 156.

The shaft 162 is preferably made from a resilient material (e.g., nickel-titanium alloy), allowing the rotation stop 160 to be moved in a generally facial direction and self-return to a generally planar configuration. The resiliency tends to hold the stop pin 164 in place and in captive relationship to the channel 156 during the course of treatment, but also enables the pin 164 to be disengaged when desired. This reversible engagement between the stop pin 164 and the channel 156 allows for different lower molar appliance connectors or connector orientations to be used during the course of treatment.

The connector 150 can be removably secured to the lower molar appliance 70 via a pin 90 including a shank that is threaded through the aperture 157 in connecting wall 154 and passage 80. The pin 90 can include an enlarged head that retains the connector 150 on the pin shank. The shank can also be bent to a generally "L"-shaped configuration and has a size that is adapted to fit within the passage 80. Once the pin shank is inserted in the passage 80, an outer end section of the shank can be bent in order to securely couple the connector 150 to the lower molar appliance 70 and the associated molar tooth. However, other types of couplers, such as links or wire loops, may be used in place of the pin 90. Alternatively, the coupling wall segment 154 (or portion of the base plate 152) may be adhered, soldered, or brazed to the lower molar appliance. When configured as shown in FIG. 5 at least a portion of the base plate 152 extends over facial surface of lower molar appliance 70 and is located in a mesial direction from the coupling wall segment 154.

The connector 150 may be secured to the outer end of the third segment 142 by the manufacturer or optionally by the practitioner. For example, it may be preferable for the manufacturer to supply the third member 142 in two or more different overall lengths in order to allow the practitioner to choose a size that would best fit the oral cavity of a particular patient. In that case, the manufacturer may elect to permanently secure a connector 150 to the distal end coupling 146 of the third segment 142.

As shown in FIGS. 1 and 2, the force module 110 is in its nearly fully compressed configuration when the patient's jaws are closed. In this nearly fully compressed configuration, the upper and lower modules 112, 140 are generally parallel to the occlusal plane of the patient and the spring 118 is almost but not fully compressed. The inherent bias of the spring 118 provides the desired corrective forces by urging the lower molar appliance in a direction toward the outer end segment 144, with the result that the lower jaw tends to shift in a forward direction relative to the upper jaw. When the patient's jaws are closed, the stop pin 164 can engage a gingival end of the channel 156, and prevents further swinging movement of the module 110 in a clockwise direction viewing FIG. 2 from its illustrated orientation.

Figure 7:
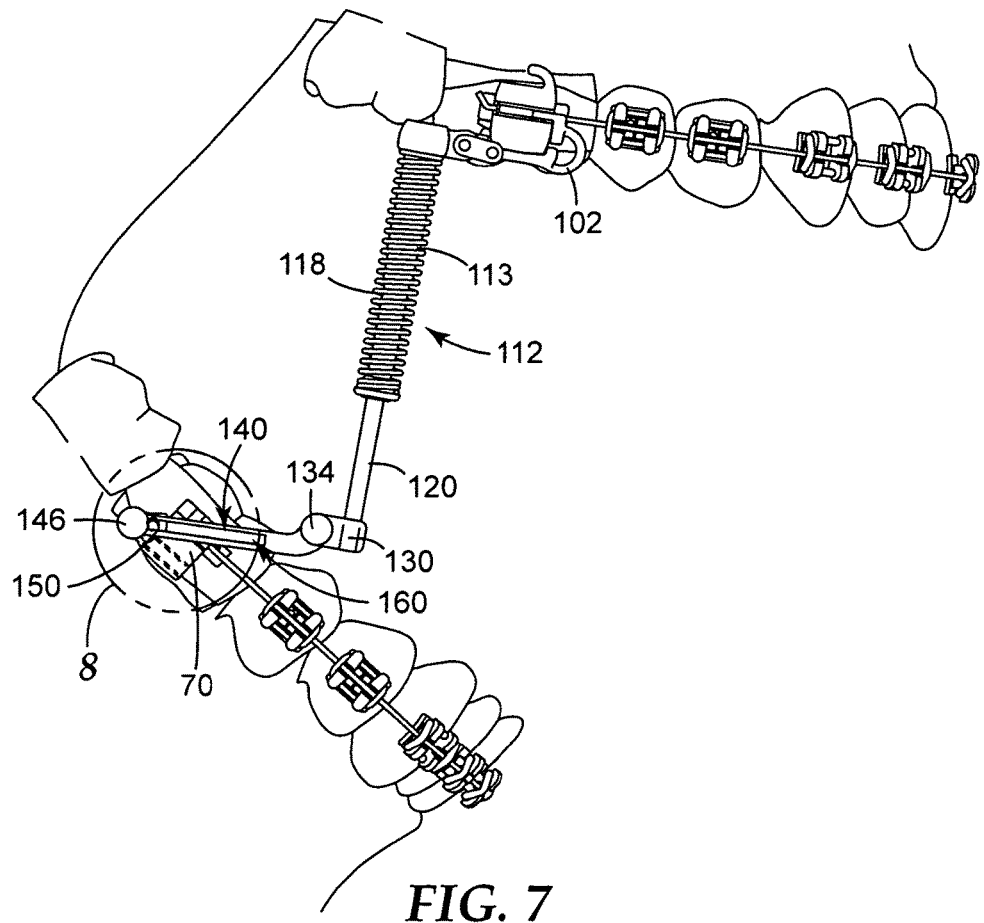
FIG. 7 is a view somewhat similar to FIG. 6 except that the patient's jaws have been fully opened.

As the patient's jaws are opened, the upper module 112 pivots relative to lower module 140 at pivot link 130, and the spring 118 begins to urge the first member 113 and the sleeve 116 in opposite directions. In the partially opened stage depicted in FIG. 6, the spring 118 has reached the end of its active range and is no longer fully compressed. Also, the lower module 140 remains generally parallel to the occlusal plane of the lower arch. As the jaws are opened yet wider as shown in FIG. 7, an enlarged inner end portion of the sleeve 116 comes into contact with the inner, narrowed end portion of the first member 113. Once such contact occurs, further widening of the patient's jaws causes the second member 120 to move in directions toward the pivot link 130, with the second member 120 is freely slidable within the sleeve 116.

Figure 8:
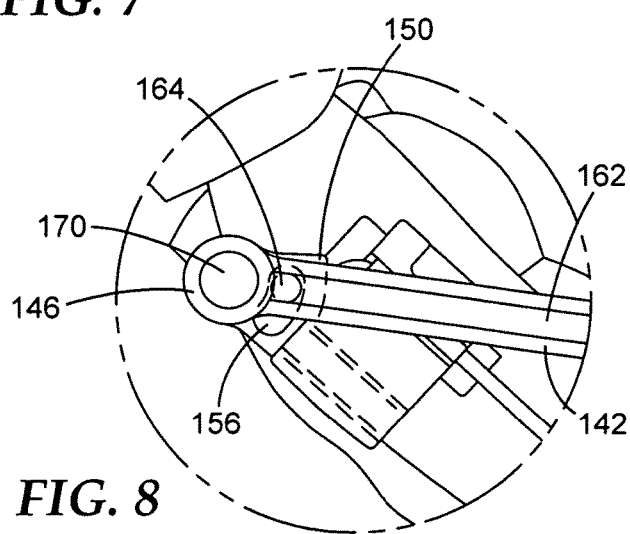
FIG. 8 is an enlarged view of FIG. 7, focusing on a lower appliance connector that may limit rotation of the intraoral force module relative to the patient's lower dental arch.

Furthermore, the third segment 142 rotates relative to connector 150 until such time as the stop pin 164 engages the occlusal end of channel 156 (as can be seen in more detail in FIG. 8). Assuming the second member 120 has reached the end of its permissible travel, the connector 150 and cooperating rotation stop 160 will serve to prevent or at least dissuade the patient from further opening the jaws. Without such a limit on third segment 142 rotation, the pivot link 130 could be thrust distally towards the back of the mouth if the patient's jaws are positioned too far apart. Such mesial-distal reversal could significantly interrupt treatment, compromise one or more components of the orthodontic assembly 100, and cause severe discomfort for the patient.

The assembly 100 accordingly provides several advantages:
1) The module is securable to both the upper and lower arch without use of an archwire or other anterior orthodontic appliances. Only molar appliances are necessary, making force module 110 particularly well suited for use with lingual braces.
2) A molar to molar attachment combined with active forces provides a more compact treatment device.
3) Module components reduce or prevent excess rotation, but still allows for the patient to open and close mouth under common circumstances without substantial irritation.

Over a period of time, the force module 110 shifts the jaws toward a permanent Class I relationship. As the position of the jaws is corrected, the spring 118 is not extended as far during jaw closure and consequently provides less force in compression. In response, the practitioner may elect to increase the effective, active length of the force module 110 to ensure that the force exerted on the patient's jaws remains effective. The effective length (and accordingly active and/or repositioning force) may be increased (or decreased if desired) by removing the force module 110 from the patient's mouth and then changing the second member 120 or the spring 118. Alternatively, the practitioner can crimp on one or more stop collars to the second member 120 in the space between the spring 118 and the pivot link 130, so that the second member 120 does not slide as far into first member 113 when the patient's jaws are closed. Suitable stop members may be found, for example, in U.S. Pat. No. 6,589,051 (Cleary), though other configurations are possible.

In certain circumstances, however, the above methods for increasing the effective length of the force module are too invasive or time consuming for the practitioner or patient. Removal of the entire force module 110 from the patient's mouth risks patient discomfort and damage to the components. Attempting to replace or add to the components pf the upper module 112 in vivo can increase the risk of mishandling components, potentially leading to accidental consumption by the patient.

Figure 9:
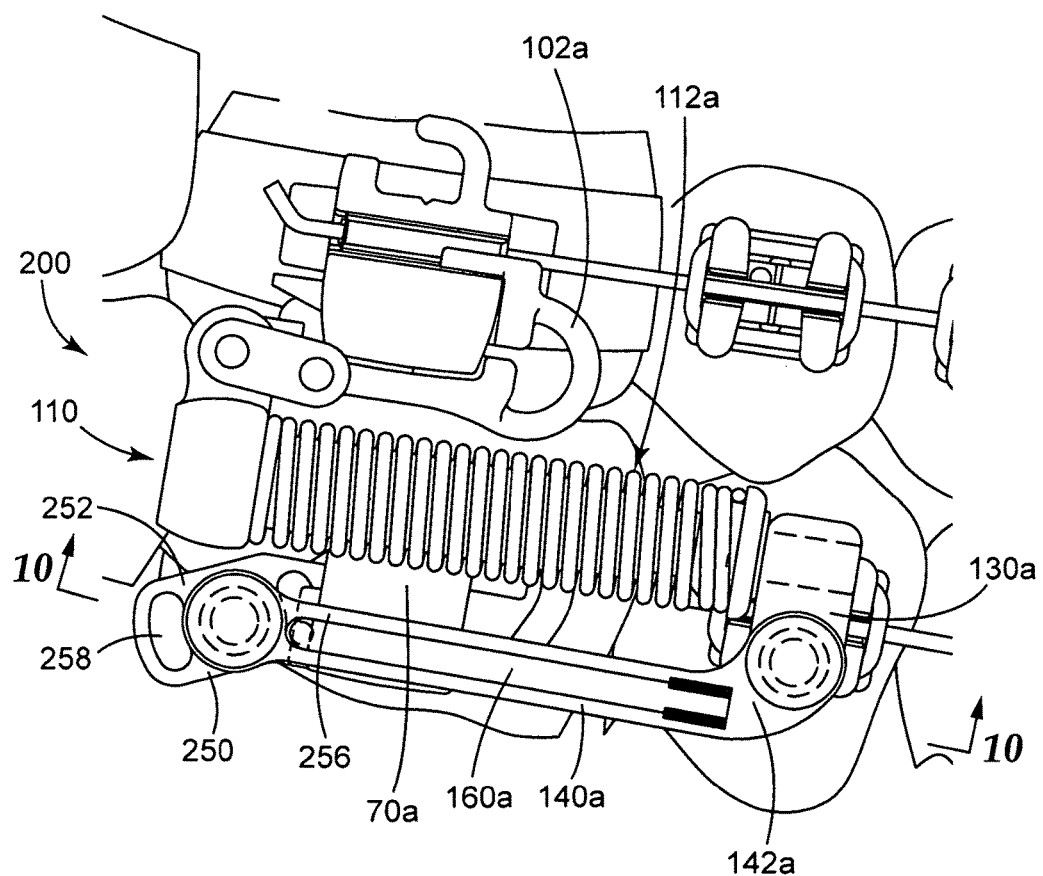
FIG. 9 is an enlarged, side elevational partial view of an exemplary upper and lower dental arch of a patient including an intraoral force module and lower appliance connector according to another embodiment of the disclosure.

FIG. 9 depicts an orthodontic assembly 200 with a force module 110*a* that includes a rotatable connector 250 configured to allow for an increase in the active length of the force module 110*a* without modification or removal of the upper module 112*a* from the mouth. The upper and lower modules 112*a*, 140*a* are essentially identical to the upper and lower modules 112, 140 described above, and other aspects of the orthodontic assembly 200 are essentially identical to the force module 110 except for certain aspects of connector 250. Those skilled in the art will accordingly perceive that functional elements of force module 110 apply mutatis mutandis to force module 110*a*, and need not be repeated at length here.

The connector 250 includes first and second arcuate channels 256, 258 in base plate 252. The first and second channels 256, 258 are positioned on either side of a central aperture 255, proximate opposing mesial-distal edge regions. Each channel 256, 258 includes occlusal and gingival ends to limit rotational movement of the third segment 142*a* in an arc about the base plate 252. The channels 256, 258 can also extend at least partially through the facial-lingual thickness of the base plate 252, though typically both have the same facial-lingual depth. The second channel 258 is disposed at a location on base plate 252 in a generally facial direction from coupling wall 254.

Figure 10:
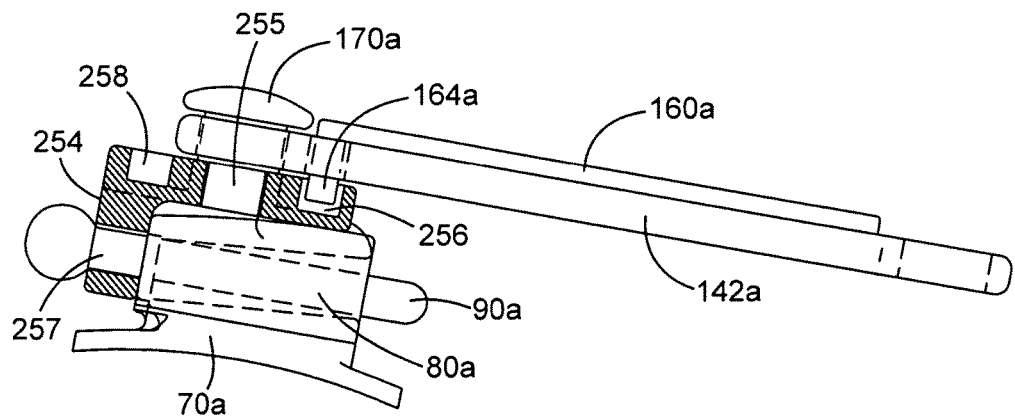
FIG. 10 is a cross-sectional view of the lower appliance connector featured in FIG. 9, coupled to both the force module and a lower molar appliance in a first orientation.
Figure 11:
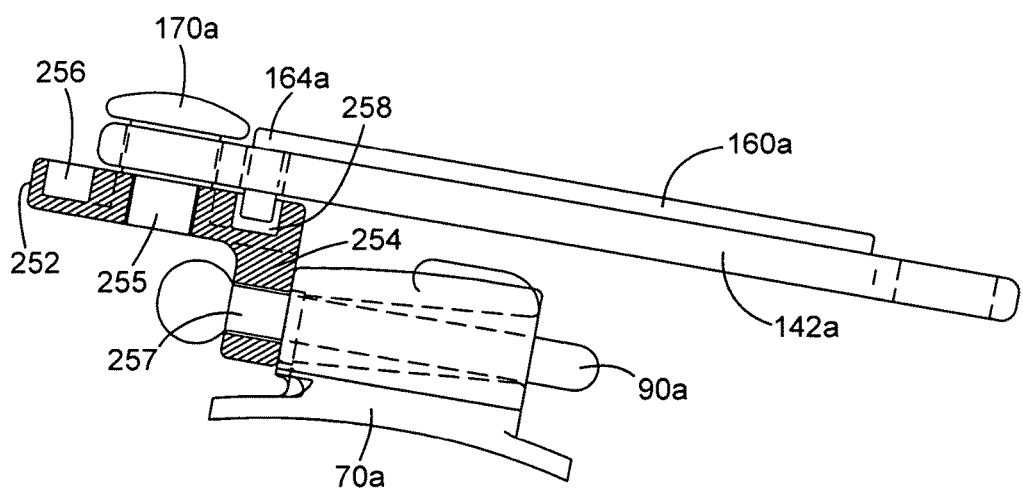
FIG. 11 is a cross-sectional view of the lower appliance connector featured in FIG. 9, coupled to both the force module and a lower molar appliance in a second orientation.

The availability of two, offsetting channels 256, 258 allows for the effective length of force module 110*a* to be increased by changing the position of the third segment 142*a* relative to lower molar appliance 70*a*. At an initial configuration shown in FIG. 10, the central aperture 255 and channel 256 extend over at least some of the facial surfaces of the lower molar appliance 70*a*, providing a connection point for the third segment 142*a* and a certain mesial distal distance between the upper and lower modules. As the position of the jaws is corrected, the activation length of the force module 110*a* may be increased by moving that connection point distally. The connector 252 may be decoupled from the lower molar appliance 70*a* by removing pin 90*a* and the rotation stop 160*a* subsequently disengaged from first arcuate channel 256. The connector is then rotated about 180 degrees such that first channel 256 is located distal to second channel 258 and the opposite surface of coupling wall segment 254 is positioned adjacent passage 80*a*. As shown in FIG. 11, once the coupling wall segment 254 is again secured relative to the passage 80*a*, the second channel 258 will be located adjacent a distal edge region of the lower molar appliance 70*a*. The stop pin 164*a* may then be engaged with second channel 258. As a result, the mesial-distal distance between the upper and lower modules is decreased, providing for continued treatment forces when the patient's jaws are closed.

Rotation of connector 250 is accordingly possible without disassembling any other component of the force module 110*a*. This simplified reactivation process reduces time needed with a patient, as the practitioner need not remove or replace the force module 110*a*. Furthermore, the potential risk to the patient is reduced, as fewer small components are disassembled and potentially free in the mouth.

Figure 12:
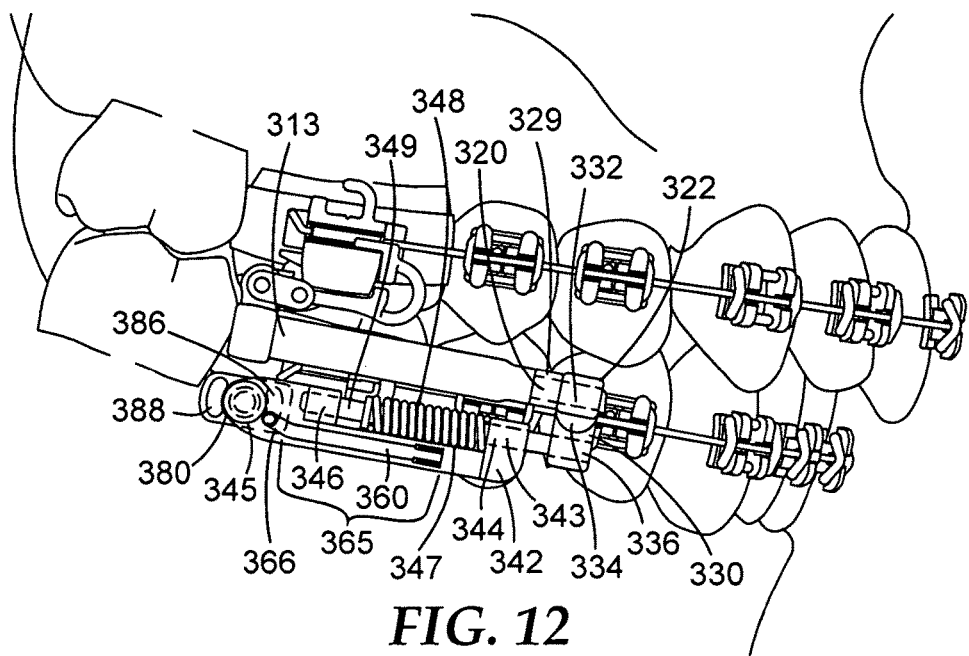
FIG. 12 is a side elevational view of a repositioning device including both an upper module and a lower module, as well as a rotatable connector, according to another embodiment of the disclosure.
Figure 13:
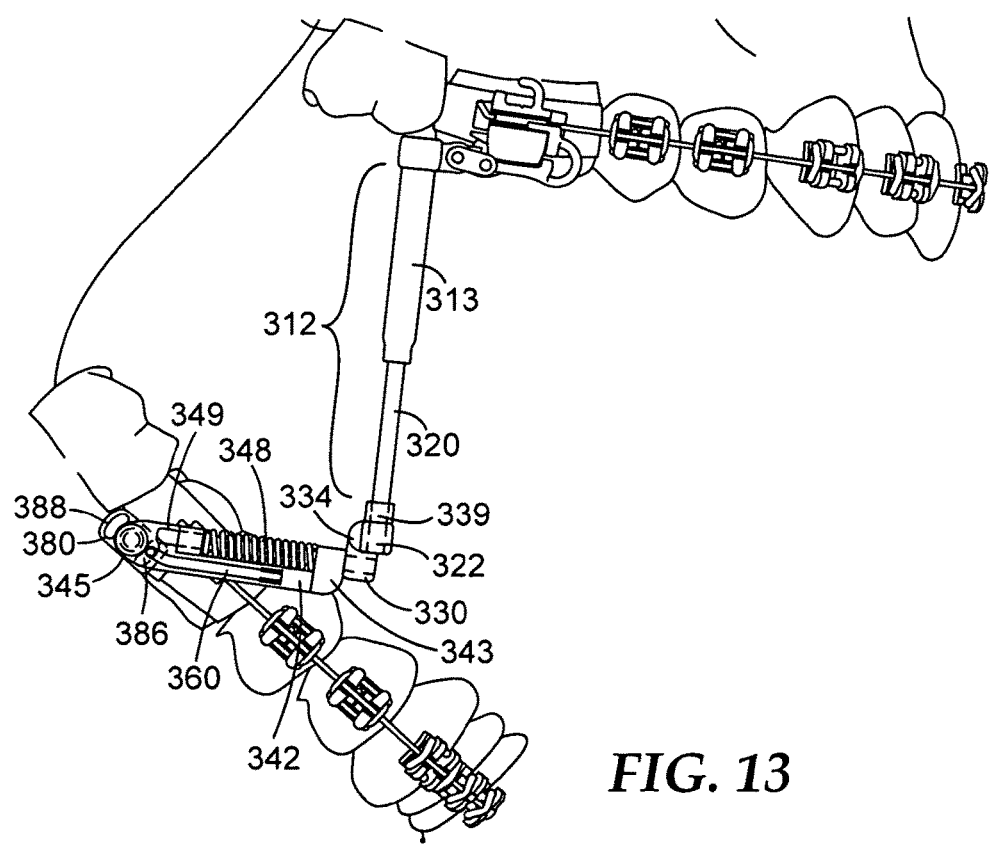
FIG. 13 is a view somewhat similar to FIG. 11 except that the patient's jaws have been fully opened.
Figure 14:
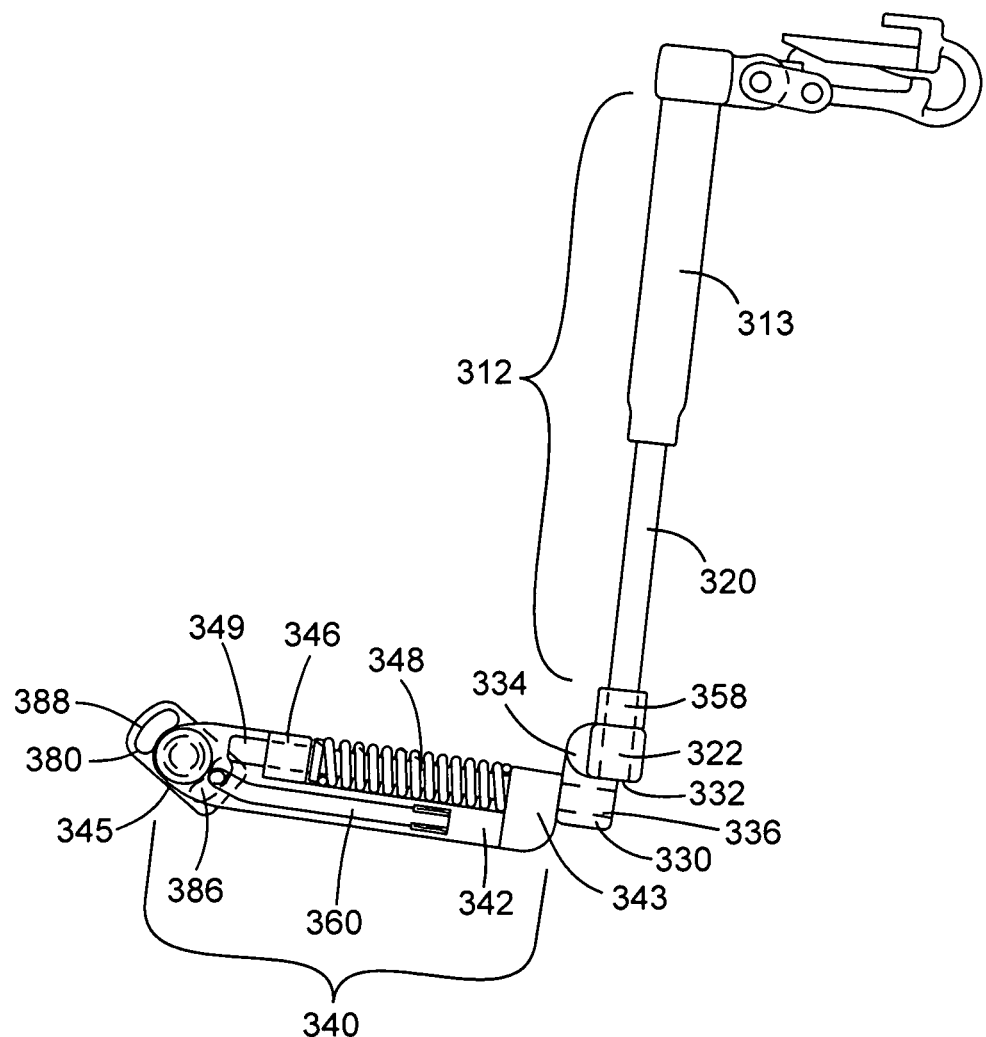
FIG. 14 is an illustration of the repositioning device of FIG. 13, with the patient's jaws and teeth omitted.

Though particularly useful for intraoral force module featuring an active, compression spring, the connectors of the present disclosure can be utilized with other repositioning devices. One such embodiment of an orthodontic assembly 300 including a mandibular repositioning device 310 and a rotatable connector 380 is depicted in FIGS. 12, 13, and 14. Those skilled in the art will perceive that functional elements of connector 250 apply mutatis mutandis to connector 380, and need not be repeated at length here. The device 310 includes an upper module 312 and a lower module 340. In the illustrated embodiment, the upper module 312 features a telescoping assembly somewhat similar to the upper module 112 in force module 110. The lower module 340 includes a spring housing 342 and a coil spring 348. The telescoping assembly may, in other embodiments, share aspects of the devices described in U.S. Pat. No. 6,988,888 (Cleary).

The telescoping assembly includes a hollow first member 313 having a tubular, elongated shape. A distal outer end portion of the first member 313 includes an end cap 314 with a coupling to enable connection of the upper module 312 to an attachment device 302. A lower end portion of the first member 313 is radially narrowed and presents an inner diameter that is less than the outer diameter of the enlarged upper end of the first member 313. The telescoping assembly also includes a second member 320 received at least partially in the first member 313 for sliding movement in a longitudinal direction along the central, longitudinal axis of the first member 313. In this embodiment, the second member 320 has a solid, circular cross-sectional configuration along its longitudinal axis, although other configurations are also possible.

A distal end portion of the second member 320 is radially enlarged in stepped fashion, such that the enlarged upper end of the second member 320 cannot slide past the lower, narrowed end portion of the first member 313 and as a result a limit to outward travel is provided. This relationship operates to retain the members in an assembled state.

In certain embodiments, the second member 320 can include one or more collars 329 that are fixed in place relative to a mesial outer end segment 322. The collar 329 can limit the extent of movement of the second member 320 by engaging the lower end of first member 313 when the patient's jaws are nearly fully compressed.

Figure 15:
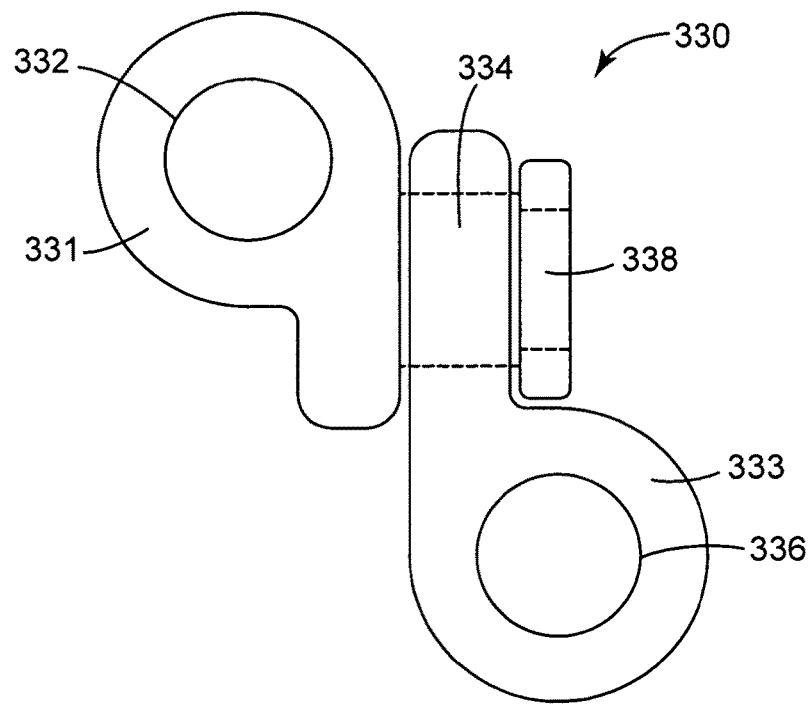
FIG. 15 is a mesial end view of a pivot link as depicted in FIGS. 12-14.

The outer mesial end 322 of the second member 320 is secured in a pivot link 330, which includes an upper segment 331 including a mesial-distal extending recess 332 and a lower segment 333 also including a mesial-distal recess 336. A hinge 334 is disposed between the segment 331, 333 and has an axis of rotation extending in a generally facial-lingual direction (i.e., generally perpendicular to the longitudinal axis of first and second members 313, 320). In the depicted embodiments, the outer mesial end 322 remains essentially fixed relative to recess 332 during use of the device 310. As best illustrated in FIG. 15, the upper and lower segments 331, 333 are offset on a facial-lingual axis from the hinge 334. Accordingly, the upper segment 331 and recess 332 are disposed in a generally facial direction from the lower segment 333 and recess 336. Hinge 334 may be created by a rivet, pin, or like structure 338 that extends through a portion of upper and lower pivot segments 331, 333. As with pivot link 130 above, other types of pivots and hinges may also be employed.

The lower module 340 includes a spring housing 342 that extends distally from the pivot link 330 along a longitudinal axis that is generally parallel to the longitudinal axis of the telescoping assembly 312 when the assembly is in the compressed configuration of FIG. 12. The mesial outer end 343 includes a recess 344 that is coaxial with a similarly dimensioned recess 346 on the distal outer end coupling 345. A coil spring 348 is disposed in the cavity 347 between the recesses 344, 346 and coaxially extends around a cylindrical plunger 349. One end of the coil spring 348 bears against the mesial outer segment 343, while the other end is adjacent a collar 350 coupled to the plunger 349. The cylindrical plunger 349 is received in both the mesial and distal recesses 344, 346 and; in presently preferred circumstances, the plunger is removably fixed in the cavity 347, though other alternatives are possible. The cylindrical plunger 349 also serves to connect the spring housing 342 to the central pivot 330, as it is fixedly received in recess 336 and renders the three recesses (336, 344, 346) generally concentric as assembled. The spring 348 is illustrated in its nearly fully compressed position in FIG. 12 and in an extended position in FIGS. 13 and 14. As can be appreciated, the spring is movable relative to both the plunger 349 and the housing 342.

The spring housing 342 includes a distal end coupling 345, which is configured to permit rotatable attachment of the lower module to the connector 380. Such connection may be accomplished through a rivet pin, threaded screw, or any other mechanism for pivotal attachment including those described above. The spring housing 342 further includes a rotation stop 360 for coupling to arcuate channels 386 and 388 in connector 380. The rotation stop 360 includes an elongated shaft 362 and a stop pin 364, though other configurations are possible. One end of the shaft 362 is secured proximate the mesial outer segment 343. A portion 365 of the shaft 362 extends along the surface of spring housing 342 parallel to and co-extensive with at least a portion of the cylindrical rod 349. A distal portion 366 of the shaft 362 extends at an angle relative to first portion 365, positioning the stop pin 364 towards the gingival end of channel 386, allowing for greater rotation of the stop pin 364 within the connector 380 when assembled.

The spring constant of the spring 348 is selected so that the spring begins to extend whenever the force exerted by the upper module 312 in a generally mesial direction exceeds a certain amount. An example of a suitable spring is a spring that begins to extend whenever the tensile forces exerted on the spring exceed approximately 0.5 lbs (0.2 kg) and, when extended by 0.1 inch (2.5 mm), exerts a tensile force of approximately 2 lbs (0.9 kg). However, springs that are stronger or weaker may also be employed in accordance with the particular treatment program and/or the particular orthodontic appliances and other components selected by the practitioner.

Advantageously, the repositioning device 310 does not provide a hard, solid stop when the jaws are closed. Instead, the spring 348 provides a gradual increase in tension force as the jaws close. Such construction helps to ensure that the forces imposed on various components of the assembly 300 are not excessive and do not cause fatigue or fracture. In addition, such construction helps ensure that the other various tooth attachments, including the brackets and the buccal tubes, remain firmly connected to the teeth.

Over a period of time, the repositioning device 310 shifts the jaws toward a permanent Class I relationship. As the position of the jaws is corrected, the spring 348 is not extended as far during jaw closure and consequently provides less force in tension. In response, the practitioner may elect to progressively reactivate the repositioning device 310 by rotating and reinstalling connector 380 as set forth above. As a result, the spring 348 thereafter is extended an increased distance when the jaws are postured in a Class II relationship and provides additional force in tension.

Figure 16:
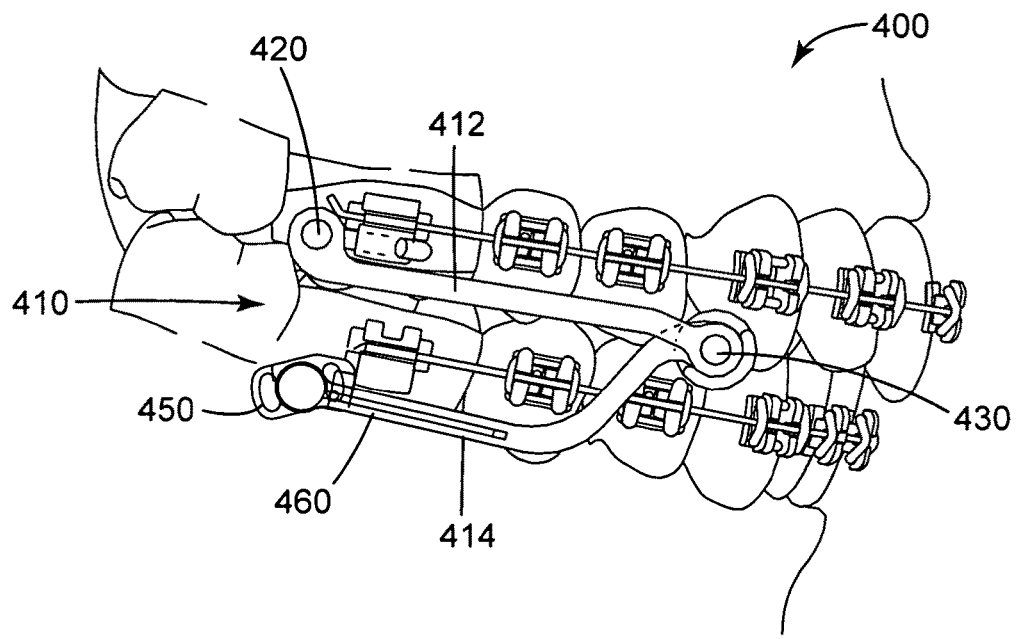
FIG. 16 is a side elevational view of a repositioning device and rotatable connector according to another embodiment of the disclosure.

Rotatable connectors of the present disclosure need not be limited to use in spring-biased force modules and repositioning devices. Another orthodontic assembly 400 including a repositioning device 410 coupled to a lower molar connector 450 is depicted in FIG. 16. Repositioning device 400, save for connector 450, is similar in most respects to the device in FIG. 1 of U.S. Pat. No. 5,980,427 (Cleary), though all other embodiments disclosed therein may be useful in the present disclosure. In summary, the repositioning device 410 includes an upper link 412 having a mesial end portion and a distal end portion, and a lower link 414 having a mesial end portion and a distal end portion. A pivot 430 connects the mesial end portion of the upper link 412 to the mesial end portion of the lower link 414. An upper connector 420 is pivotally coupled to the distal end portion of the upper link, and the lower, rotatable connector 450 is pivotally coupled to the distal end portion of the lower link 414. Rotatable connector 450 includes all of the features of rotatable connector 250, as described above. The upper link 412 and the lower link 414 each have a length sufficient to urge one jaw forward relative to the other jaw when the jaws are closed. A rotation stop 460 on lower link 414 prevents excess rotation of the lower link relative to a lower molar appliance, both when the patient's jaws are opened and closed.

Components of the assemblies 100, 200, 300, and 400 may be manufactured according to any number of methods known to the skilled artisan. These methods include, but are not limited to, milling, investment casting, metal injection molding, and rapid prototyping. In presently preferred circumstances, all of the elements of the force modules and repositioning devices (including connectors, rotatable or otherwise) of the present disclosure are made of corrosion resistant materials that provide satisfactory service in the oral environment. Suitable materials include, for example, stainless steels such as AISI 300 series types (including 302 or 304), although other materials may also be employed, such as ceramics, polymers, or composites. If polymeric components are used, these may optionally be formed by milling, injection molding, extrusion or additive manufacturing. Examples of suitable additive manufacturing processes include solid freeform fabrication such as 3D printing processes, stereolithography methods, fused deposition modeling, laminated object manufacturing, laser engineered net shaping, selective laser sintering, shape deposition manufacturing, selective laser melting, and solid ground curing. An example of a suitable 3D printing machine is the Eden brand 500V printer from Objet Geometries Ltd., using FullCure 720 acrylic-based photopolymer printing material (also available from Objet Geometries Ltd.).

Although not shown in the drawings, the force modules, repositioning devices, and attendant orthodontic assemblies described herein are normally used in pairs. While the figures depict the orthodontic assemblies in place along the right side of a patient's oral cavity, a second assembly that is similar to the depicted orthodontic assemblies in mirror image is typically installed along the left side of the patient's oral cavity. In this manner, a balanced amount of force is presented along both sides of the patient's jaws for repositioning the dental arches as desired.

In further alternative embodiments, one or more of the orthodontic correctors above are adapted to correct a Class III malocclusion. Such correction may be achieved, for example, by connecting one end of the assembly to a rotatable connector secured an upper molar appliance and the other end of the assembly to a lower molar appliance. As before, the connections between components benefit from the increased robustness and functionality provided by the present disclosure.

Embodiments

1. An intraoral force module configured for moving the relative positions of upper and lower dental arches, the force module comprising: a first member having a first outer end portion and coupled to a helical compression spring coaxial with at least a portion of said first member, the first member having a length extending in a generally mesial direction; a second member connected to the first member and pivotally movable relative to the first member in directions along a reference axis, a portion of the second member extending distally to a second outer end portion along a portion of the length of the first member; and a rotatable first connector connected to the second outer end portion of the second member, wherein the second member is movable in an arc relative to the first connector about a first axis that is generally perpendicular to the reference axis, and wherein the connector is rotatable between a first orientation and a second orientation, the second orientation providing for a more distal location of the outer end portion relative to the first orientation.

2. The force module of embodiment 1, wherein the rotatable first connector includes a first channel having an arcuate axis, the channel defining an axis of rotation for the outer end portion of the second member.

3. The force module of embodiment 2, wherein the axis of rotation is along an arc of no greater than 60 degrees, such that both the first member and the second member are substantially parallel to an occlusal plane of the lower dental arch.

4. The force module of embodiment 3, wherein the arc is no greater than 50 degrees.

5. The force module of any of the previous embodiments, wherein the spring includes a first activation force in the first orientation and a second activation force in the second orientation, and wherein the activation force in the second orientation is greater than the activation force in the first orientation.

6. The force module of embodiment 2, wherein the second member includes a rotation stop received in the channel.

7. The force module of embodiment 6, wherein the rotation stop includes a shaft and a stop pin, and wherein the shaft is resiliently attached to the second member and the stop pin is configured for receipt in the channel, and wherein movement of the shaft is in a generally buccal direction disengages the stop pin from the channel.

8. The force module of embodiment 2, wherein the connector further includes a second channel having an arcuate axis and an aperture, wherein the aperture is disposed between the first and second channel.

9. The force module of embodiment 8, wherein the first and second channels are disposed on opposing edge regions of the connector.

10. The force module of embodiment 9, wherein facial entrances to the first and second channels are substantially coplanar within a first reference plane.

11. The force module of embodiments 8-10, wherein the second member and connector are pivotally coupled through a hinge pin received in the aperture.

12. The force of module of embodiment 11, wherein the connector includes a wall segment extending in a direction generally orthogonal to the reference plane, the wall segment including a coupling portion for attachment to an orthodontic molar appliance.

13. The force module of embodiment 12, wherein the wall segment includes a passage for receipt of a connecting pin.

14. The force module of embodiment 13, wherein alignment of the passage and a recess of the orthodontic molar appliance allows the connecting pin to attach the first connector to the molar appliance.

15. The force module of embodiment 8, wherein the first channel is mesial to the second channel in the first orientation, and wherein the second channel is mesial to the first channel in the second orientation.

16. A method for modifying the active or repositioning force of an intraoral force module, the method comprising:
   providing a force module comprising a first member having a first outer end portion, the first member having a length extending in a generally mesial direction, a second member connected to the first member and pivotally movable relative to the first member in directions along a reference axis, a portion of the second member extending distally to a second outer end portion along a portion of the length of the first member, and a rotatable first connector connected to the second outer end portion of the second member and including first and second channels disposed adjacent opposing edge regions of connector, wherein the second member is movable in an arc relative to the first connector about a first axis that is generally perpendicular to the reference axis, and wherein the second member includes a rotation stop received in the first channel in the first connector;
   disengaging the rotation stop from the first channel;
   rotating the connector to a second orientation whereby the first channel is rotated to a position distal to the second channel;
   and securing the rotation stop in the second channel.

17. The method of embodiment 16, and wherein the rotation stop includes a shaft and a stop pin received in the first channel, and wherein the disengaging the rotation stop includes the act of moving the shaft in a generally facial direction to remove the stop pin from the channel.

18. The method of embodiment 16, wherein the upper module further comprises a helical compression spring coupled to and coaxial with at least a portion of said first member.

19. The method of embodiment 18, wherein the spring includes a first active force when rotation stop is received in the first channel, and wherein the spring includes a second active force when rotation stop is received in the second channel, and wherein the second active force is greater than the first active force.

20. An intraoral force module configured for moving the relative positions of upper and lower dental arches, the force module comprising:
   a first member having a first outer end portion, the first member having a length extending in a generally mesial direction;
   a second member connected to the first member and pivotally movable relative to the first member in directions along a reference axis, a portion of the second member extending distally to a second outer end portion along a portion of the length of the first member; and a first connector connected to the second outer end portion of the second member, wherein the second member is movable in an arc relative to the first connector about a first axis that is generally perpendicular to the reference axis, and wherein the connector is moveable between a first orientation and a second orientation, wherein the force module has a first active force in the first orientation and second active force in the second orientation.

21. The force module of embodiment 20, wherein the first active force is greater than the second active force.

22. The force module of embodiment 20, wherein the first active force is less than the second active force.

23. The force module of embodiments 20 or 22, wherein force module further comprises a helical compression spring coupled to and coaxial with at least a portion of said first member, wherein the spring includes a first active force when rotation stop is received in the first channel, and wherein the spring includes a second active force when rotation stop is received in the second channel, and wherein the second active force is greater than the first active force.

24. The force module of embodiment 20, wherein the first connector is rotatable.

25. The force module of embodiment 20, wherein the first connector includes first and second channels disposed on opposing edge regions of the connector, the first and second channels each including an arcuate axis.

26. A method for modifying the activation force of an intraoral force module, the method comprising:

providing a force module comprising a first member having a first outer end portion, the first member having a length extending in a generally mesial direction, a second member connected to the first member and pivotally movable relative to the first member in directions along a reference axis, a portion of the second member extending distally to a second outer end portion along a portion of the length of the first member, and a first connector connected to the second outer end portion of the second member and including first and second channels separated by a channel distance adjacent opposing edge regions of connector, wherein the second member is movable in an arc relative to the first connector about a first axis that is generally perpendicular to the reference axis, and wherein the second member includes a removable first rotation stop having a first length received in the first channel in the first connector;

providing a second rotation stop having a second length;

disengaging the first rotation stop from the first channel and the second member; and securing the second rotation stop in the second channel and on the second member.

27. The method of embodiment 26, wherein the difference between the first length of the first rotation stop and the second length of the second rotation stop is equal to the channel distance.

28. An intraoral assembly configured for moving the relative positions of upper and lower dental arches, the assembly comprising:

a first orthodontic molar appliance adapted for connection to a tooth; and a repositioning device comprising an upper module pivotally coupled to a lower module, wherein the upper module including a telescoping assembly having a first member and a second member slidably coupled to the first member for movement along a reference axis, the second member having an outer end portion, the lower module including a housing defining a cavity, a portion of the housing extending distally to a second outer end portion along a portion of the length of the telescoping assembly, wherein the housing segment includes a tension member received in the cavity, and wherein the tension member is in tension and extends in length as the upper and lower dental arches are closed.

29. The intraoral assembly of embodiment 28, wherein the tension member is a coil spring.

30. The intraoral assembly of embodiment 29, wherein the housing further includes a cylindrical plunger received in the cavity, and wherein the tension member is coaxial with the plunger.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

I claim:

1. An intraoral force module configured for moving the relative positions of upper and lower dental arches, the force module comprising:

a first member having a first outer end portion and coupled to a helical compression spring coaxial with at least a portion of said first member, the first member having a length extending in a generally mesial direction when the force module is in a closed position;

a second member connected to the first member and pivotally movable relative to the first member in directions along a reference axis, a portion of the second member extending distally to a second outer end portion along a portion of the length of the first member when the force module is in the closed position; and a rotatable lower connector connected to the second outer end portion, wherein the rotatable lower connector includes a first channel having an arcuate axis, the first channel defining an axis of rotation for the second outer end portion, wherein the second member is movable in an arc relative to the lower connector about a first axis that is generally perpendicular to the reference axis, and wherein the lower connector is rotatable between a first orientation and a second orientation, the second orientation providing for a more distal location of the second outer end portion relative to the first orientation.

2. The force module of claim 1, wherein the axis of rotation is along an arc of no greater than 60 degrees, such that both the first member and the second member are substantially parallel to an occlusal plane of the lower dental arch.

3. The force module of claim 1, wherein the spring includes an activation force in the first orientation and a second activation force in the second orientation, and wherein the activation force in the second orientation is greater than the activation force in the first orientation.

4. The force module of claim 1, wherein the second member includes a rotation stop received in the first channel, wherein the rotation stop includes a shaft and a stop pin, and wherein the shaft is resiliently attached to the second member and the stop pin is configured for receipt in the first channel, and wherein movement of the shaft is in a generally buccal direction disengages the stop pin from the first channel.

5. The force module of claim 1 wherein the lower connector further includes a second channel having an arcuate axis and an aperture, wherein the aperture is disposed between the first and second channel.

6. The force module of claim 5, wherein the first and second channels are disposed on opposing edge regions of the connector.

7. The force module of claim 6, wherein entrances to the first and second channels are substantially coplanar within a first reference plane.

8. The force of module of claim 1, wherein the connector includes a wall segment extending in a direction generally orthogonal to the reference plane, the wall segment including a coupling portion for attachment to an orthodontic molar appliance.

9. The force module of claim 8, wherein the wall segment includes a passage for receipt of a connecting pin, and wherein alignment of the passage and a recess of the orthodontic molar appliance allows the connecting pin to attach the lower connector to the molar appliance.

10. The force module of claim 5, wherein the first channel is mesial to the second channel in the first orientation, and wherein the second channel is mesial to the first channel in the second orientation.

11. An intraoral force module configured for moving the relative positions of upper and lower dental arches, the force module comprising:
   a first member having a first outer end portion, the first member having a length extending in a generally mesial direction when the force module is in the closed position;
   a second member connected to the first member and pivotally movable relative to the first member in directions along a reference axis, a portion of the second member extending distally to a second outer end portion along a portion of the length of the first member when the force module is in the closed position; and
   a lower connector, wherein the lower connector is rotatable, and wherein the lower connector includes a first channel and a second channel, the first and second channels disposed on opposing edge regions of the connector, the first and second channels each including an arcuate axis, wherein the lower connector is connected to the second outer end portion of the second member, wherein the second member is movable in an arc relative to the lower connector about a first axis that is generally perpendicular to the reference axis, and wherein the lower connector is moveable between a first orientation and a second orientation, wherein the force module has a first active force in the first orientation and second active force in the second orientation.

12. The force module of claim 11, wherein the first active force is greater than the second active force.

13. The force module of claim 11, wherein the first active force is less than the second active force.

* * * * *